US012661839B1

(12) United States Patent
Chang et al.

(10) Patent No.: US 12,661,839 B1
(45) Date of Patent: **\*Jun. 23, 2026**

(54) SYSTEM AND METHOD FOR PREDICTING WARPING BEHAVIOR IN A PRODUCT

(71) Applicant: CORETECH SYSTEM CO., LTD., Hsinchu County (TW)

(72) Inventors: Hsi-Hung Chang, New Taipei City (TW); Chih-Chung Hsu, Hsinchu County (TW); Hsien-Sen Chiu, Hsinchu City (TW); Chia-Hsiang Hsu, Hsinchu County (TW)

(73) Assignee: CORETECH SYSTEM CO., LTD., Hsinchu County (TW)

( \* ) Notice: Subject to any disclaimer, the term of this patent is extended or adjusted under 35 U.S.C. 154(b) by 0 days.

This patent is subject to a terminal disclaimer.

(21) Appl. No.: 19/260,277

(22) Filed: Jul. 3, 2025

(51) Int. Cl.
  *B29C 45/76* (2006.01)
  *G06F 30/20* (2020.01)
  *G16C 60/00* (2019.01)

(52) U.S. Cl.
  CPC ............ *B29C 45/766* (2013.01); *G06F 30/20* (2020.01); *G16C 60/00* (2019.02); *B29C 2945/76434* (2013.01); *B29C 2945/76929* (2013.01)

(58) Field of Classification Search
  CPC ...................................................... B29C 45/766
  USPC ........................................................ 264/40.1
  See application file for complete search history.

(56) References Cited

U.S. PATENT DOCUMENTS

2023/0347564 A1\* 11/2023 Wollny ................. B29C 45/766

\* cited by examiner

*Primary Examiner* — Jacob T Minskey
(74) *Attorney, Agent, or Firm* — Winston Hsu

(57) ABSTRACT

A method for predicting warping behavior in a product involves: 1) acquiring experimental warping data from a specimen under predetermined molding conditions, 2) generating simulated warping data using a digital twin, 3) calculating strain/stress components of both experimental and simulated data, 4) performing regression analysis to establish conversion relationships between experimental and simulated strains in transverse/parallel directions, and 5) generating calibrated simulation predictions using the derived relationships.

12 Claims, 13 Drawing Sheets
(6 of 13 Drawing Sheet(s) Filed in Color)

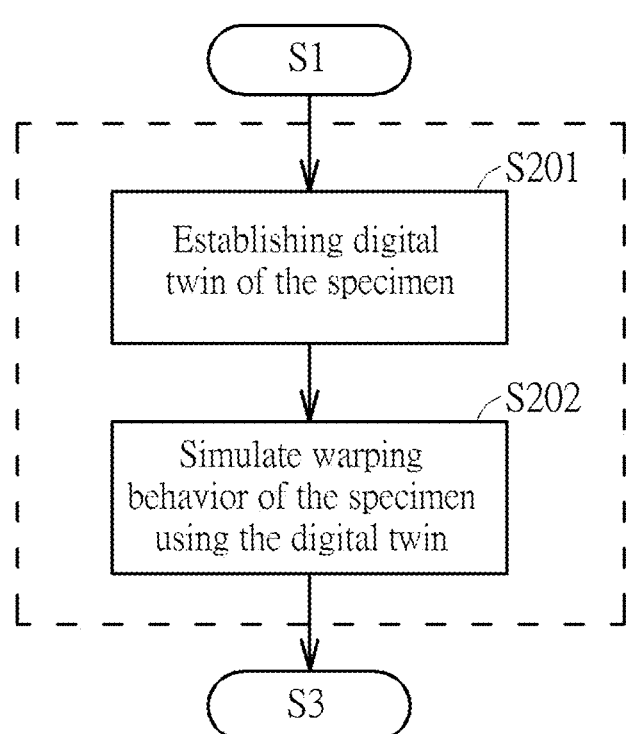
S1
Establishing digital
twin of the specimen ⟋S201
Simulate warping
behavior of the specimen
using the digital twin ⟋S202
S3
FIG. 5

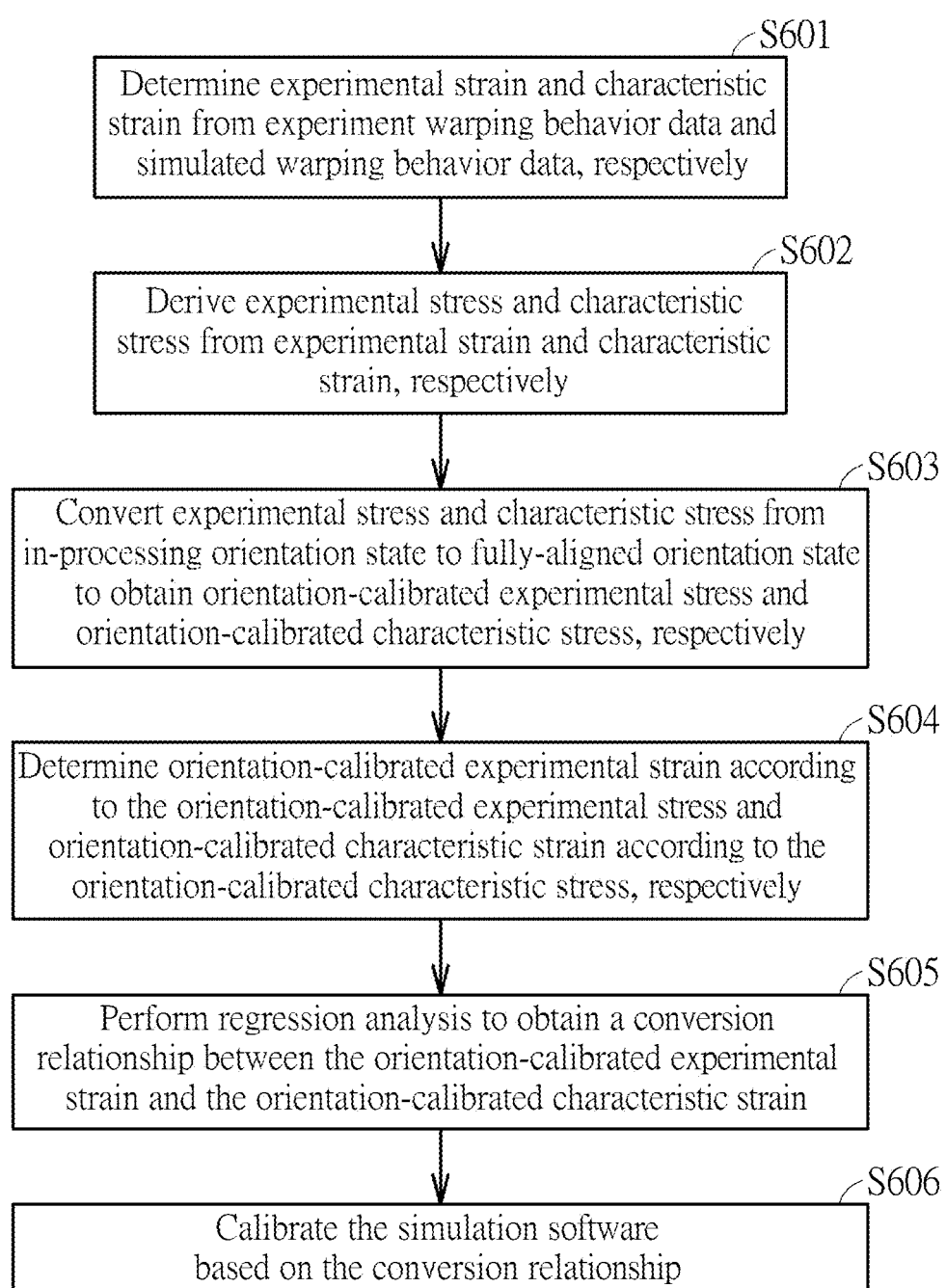

S601

Determine experimental strain and characteristic strain from experiment warping behavior data and simulated warping behavior data, respectively

S602

Derive experimental stress and characteristic stress from experimental strain and characteristic strain, respectively

S603

Convert experimental stress and characteristic stress from in-processing orientation state to fully-aligned orientation state to obtain orientation-calibrated experimental stress and orientation-calibrated characteristic stress, respectively

S604

Determine orientation-calibrated experimental strain according to the orientation-calibrated experimental stress and orientation-calibrated characteristic strain according to the orientation-calibrated characteristic stress, respectively

S605

Perform regression analysis to obtain a conversion relationship between the orientation-calibrated experimental strain and the orientation-calibrated characteristic strain

S606

Calibrate the simulation software based on the conversion relationship

FIG. 6

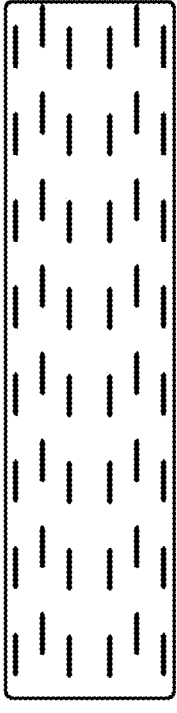
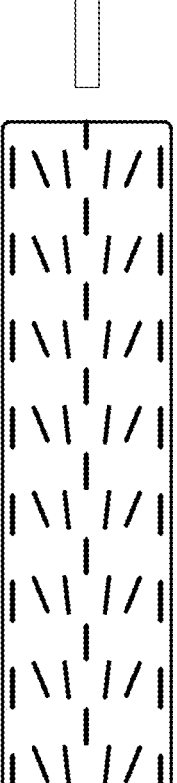
FIG. 8

SYSTEM AND METHOD FOR PREDICTING WARPING BEHAVIOR IN A PRODUCT

BACKGROUND OF THE INVENTION

1. Field of the Invention

The invention relates to a simulation technique for molding system, and more particularly to a system and a method for predicting warping behavior in an injection-molded product.

2. Description of the Prior Art

In the field of injection-molding techniques, various technologies have been developed to enhance the accuracy and efficiency of simulating warping behaviors of materials. However, there is still a lot to be desired regarding remedying discrepancies between predicted and actual outcomes.

For example, existing simulation means often lacks consideration for individual effects affecting the final warping behavior of a given material during simulation, thus causing the predicted outcome far off from the actual warping behavior. Further, existing simulation means lacks ability to isolate individual effects from one another during simulation, making the predicted final warping behavior far off from actual result. Furthermore, existing simulation means only operate with set parameters, but lacks calibration flexibility with respect to actual operational needs. Moreover, existing simulation means require massive dataset from user to achieve simulation accuracy, meaning a huge experiment cost is required before the simulation means is put into practice.

SUMMARY OF THE INVENTION

To address the aforementioned issues, provided is a method for predicting warping behavior in a product, including: acquiring, via an injection-molding apparatus, an experiment warping behavior data of a specimen of the product under a predetermined molding condition; establishing, via a simulation software, a digital twin of the specimen; generating, via the simulation software, a simulated warping behavior data of the specimen under the predetermined molding condition using the digital twin; determining, via the simulation software, an experimental strain in a principal coordinate system from the experiment warping behavior data; determining, via the simulation software, a characteristic strain in the principal coordinate system from the simulated warping behavior data; deriving, via the simulation software, an experimental stress in the principal coordinate system from the experimental strain; deriving, via the simulation software, a characteristic stress in the principal coordinate system from the characteristic strain; converting, via the simulation software, the experimental stress to a fully-aligned orientation state to obtain an orientation-calibrated experimental stress at a transverse direction of a pseudo coordinate system of the specimen and an orientation-calibrated experimental stress at a parallel direction of the pseudo coordinate system of the specimen; converting, via the simulation software, the characteristic stress to the fully-aligned orientation state to obtain an orientation-calibrated characteristic stress at the transverse direction and an orientation-calibrated characteristic stress at the parallel direction; determining, via the simulation software, an orientation-calibrated experimental strain at the transverse direction and an orientation-calibrated experimental strain at the parallel direction according to the orientation-calibrated experimental stress at the transverse direction and the orientation-calibrated experimental stress at the parallel direction, respectively; determining, via the simulation software, an orientation-calibrated characteristic strain at the transverse direction and an orientation-calibrated characteristic strain at the parallel direction according to the orientation-calibrated characteristic stress at the transverse direction and the orientation-calibrated characteristic stress at the parallel direction, respectively; and performing, via the simulation software, a regression analysis to obtain a conversion relationship between the orientation-calibrated experimental strain and the orientation-calibrated characteristic strain at the transverse direction and between the orientation-calibrated experimental strain and the orientation-calibrated characteristic strain at the parallel direction; and generating, via the simulation software, a calibrated-simulated warping behavior data of the specimen under the predetermined molding condition using the digital twin according to the conversion relationship.

Further provided is a system for predicting warping behavior in a product, including an injection-molding apparatus configured to carry out molding process of a product and monitoring operating conditions during molding of the product, and a computer coupled with the injection-molding apparatus, and carrying a simulation software. The simulation software is configured for, when being executed by the computer, simulating the molding conditions of the product according to the operating conditions of the injection-molding apparatus, predetermined molding conditions, and/or given molding conditions.

Based on the above, the present disclosure at least achieves the following technical effects:

1. To enable product quality assurance through warpage prediction in injection-molded polymer components, the present disclosure takes complex interactions between material behavior, thermal gradients, and internal stress development during the molding process (e.g., melt filling, packing, cooling, and structural deformation) into consideration to analyze effects that influence the final part geometry, so as to simulate these effects accurately and provide quantitative predictions of post-molding deformation based on the process history and material characteristics.

2. Accurate warpage prediction of the present disclosure may be contributed by modeling orientations and their effects on material anisotropy. For example, in fiber-reinforced polymers, flow-induced orientation occurs as fibers align with the melt flow during cavity filling. This orientation significantly alters local mechanical stiffness and shrinkage behavior, making the polymer matrix behave anisotropically. To account for these effects, the orientation state (described as orientation tensors hereafter) is computed during the flow stage of injection molding and may be subsequently mapped into the structural deformation stage. Incorporating this orientation-dependent material behavior into the stress and shrinkage calculations allows the analysis to reflect realistic, directionally-dependent warpage behavior. Therefore, modeling of orientation tensors is critical to avoid underprediction or misrepresentation of deformation in fiber-filled parts.

3. In addition to the orientations, internal residual stresses play a decisive role in post-molding warpage. These stresses develop due to non-uniform solidification and cooling across the part thickness. Differential cooling leads to spatial variations in shrinkage and internal constraint, resulting in frozen-in stress fields. There-fore, the present disclosure proposes a more accurate methodology that involves computing the complete residual stress field derived from the cooling history. These stresses act as internal loads in the final defor-mation analysis and must be carried forward with fidelity from thermal analysis stages. Their influence on part deformation can be substantial, especially in thick or geometrically complex components.

4. To improve prediction accuracy, the present disclosure integrates both characteristic orientation effects and residual stress evolution into a unified, sequential simu-lation framework. The methodology ensures that the orientation-dependent anisotropic properties and the stress fields from thermal gradients are coherently transferred and applied in the structural warpage cal-culation. By structuring the workflow to maintain con-tinuity of physical parameters across each stage of the simulation, the approach enhances predictive reliabil-ity.

5. The present disclosure is compatible with arbitrary standard computer aided engineering environments capable of multi-physics simulation, where the core innovation resides in the procedural coupling and data integration that governs the accuracy of final warpage results.

The objectives of the present disclosure will no doubt become readily understandable to those of ordinary skill in the art after reading the following detailed description of the embodiments that are illustrated in the various figures and drawings.

BRIEF DESCRIPTION OF THE DRAWINGS

The patent or application file contains at least one drawing executed in color. Copies of this patent or patent application publication with color drawing (s) will be provided by the Office upon request and payment of the necessary fee.

FIG. 5 is a detailed flow diagram of the method for predicting the warping behavior according to at least one embodiment of the present disclosure.

FIG. 6 is a detailed flow diagram of the method for predicting the warping behavior according to at least one embodiment of the present disclosure.

FIG. 8 is a schematic diagram showing conversion of a physical quantity under a weakly-aligned in-processing state into an equivalent quantity under a fully-aligned orientation state according to at least one embodiment of the present disclosure.

DETAILED DESCRIPTION

The following descriptions of the embodiments illustrate implementations of the present invention, and those skilled in the art of the present invention can readily understand the advantages and effects of the present invention and/or apply the present invention to other embodiments in accordance with the contents herein. Therefore, any factors described in the present invention may be combined with any other factors disclosed in embodiments of the present invention.

The orders of drawings shown in accompanying drawings of this disclosure are only used to illustrate embodiments described herein, such that those with ordinary skill in the art can read and understand the present invention therefrom, of which are not intended to limit the scope of this disclosure. Any changes, modifications, or adjustments of said features, without affecting the designed purposes and effects of the present invention, should all fall within the scope of tech-nical content of this disclosure.

As used herein, when describing an object "comprises," "includes" or "has" a limitation, unless otherwise specified, it may additionally encompass other elements, structures, regions, parts, apparatus, devices, systems, steps, connec-tions, modules, units, etc., and should not exclude others. Further, unless otherwise specified, wordings in singular forms such as "a," "an" and "the" also pertain to plural forms, and wordings such as "or" and "and/or" may be used interchangeably.

Figure 1:
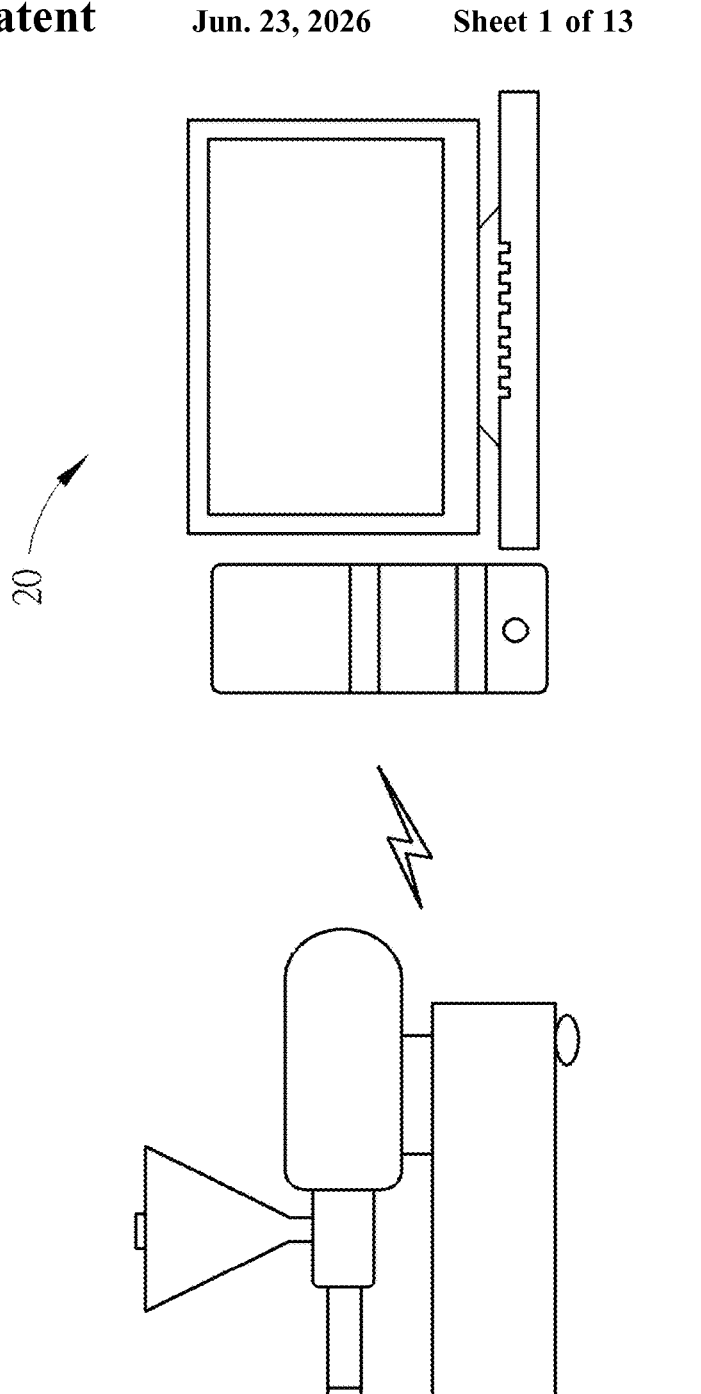
FIG. 1 is a schematic diagram of operating environment for the method for predicting warping behavior in a product according to at least one embodiment of the present disclo-sure.

FIG. 1 is a schematic diagram of operating environment for the method for predicting warping behavior in a product. Here, an injection-molding apparatus 10 may be used to carry out molding process of a product and monitoring operating conditions during molding of the product. Further, the injection-molding apparatus 10 may be coupled with a computer 20 carrying a simulation software for, when being executed by the computer 20, simulating the molding con-ditions of the product according to the operating conditions of the injection-molding apparatus 10, predetermined mold-ing conditions and/or given molding conditions different from the predetermined molding conditions. The simulation software may be a computer-assisted engineering (CAE) simulation software. The computer 20 can be a desktop computer, a laptop computer, a tablet computer, or a cellular phone. In addition, the computer 20 and the injection-molding apparatus 10 can interact using wired links, wireless links, a combination thereof, or any other known or later developed elements that are capable of supplying and/or communicating data to and from the connected computer 20 and the injection-molding apparatus 10.

Figure 2:
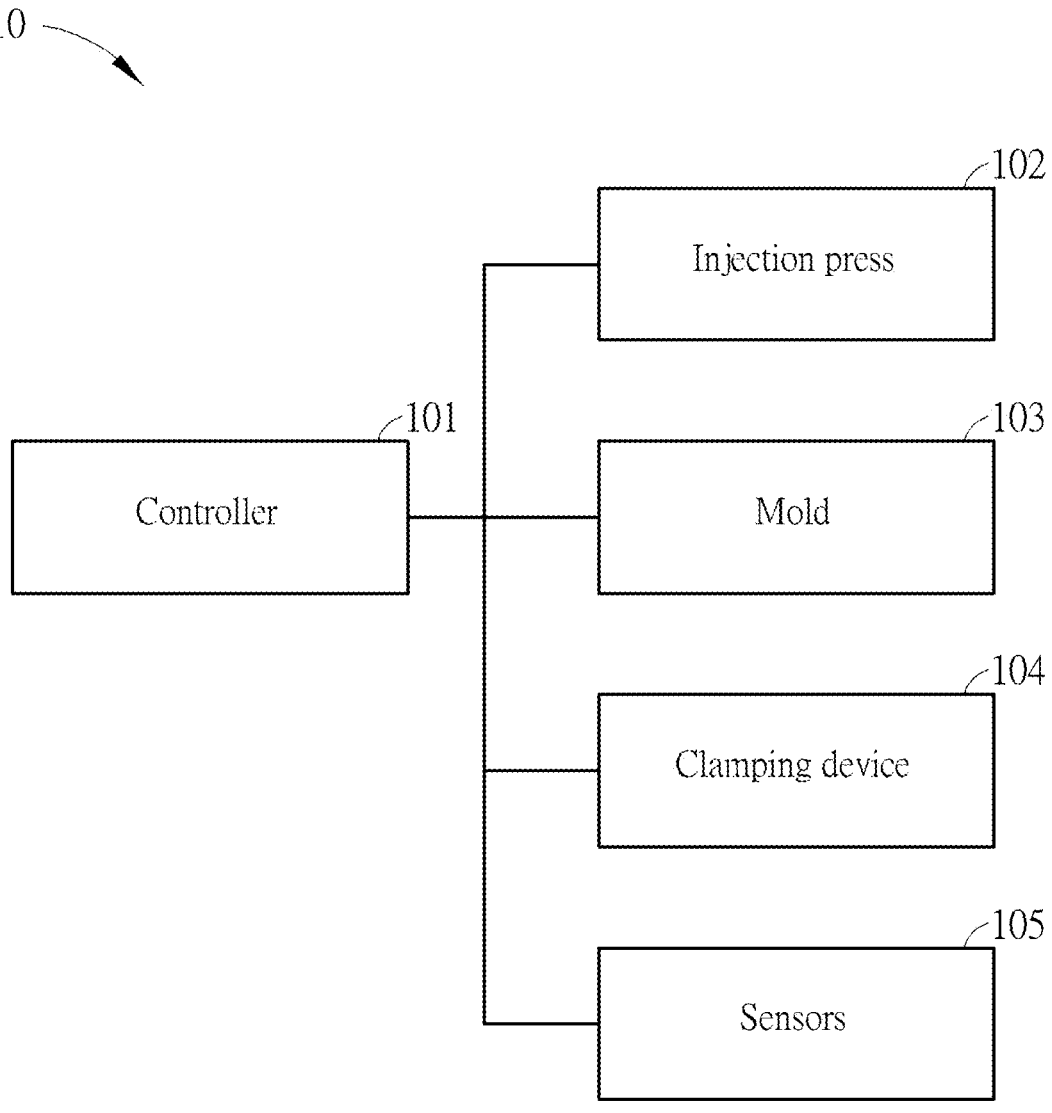
FIG. 2 is a schematic diagram of the injection-molding apparatus according to at least one embodiment of the present disclosure.

FIG. 2 is a schematic diagram of the injection-molding apparatus 10 according to at least one embodiments of the present disclosure. Here, the injection-molding apparatus 10 may at least include, among other peripheral devices, an injection press 102 for pressing out material for molding the product, a mold 103 for accommodating the material pressed out by the injection press 102, a clamping device 104 for securing the mold 103 while waiting for the material in the mold to cure and take one desired shape of the product, at least one sensor 105 for monitoring the operating conditions during molding, and a controller 101 interfacing with and controlling operations of the injection press 102, the mold 103, the clamping device 104 and the sensors 105.

Figure 3:
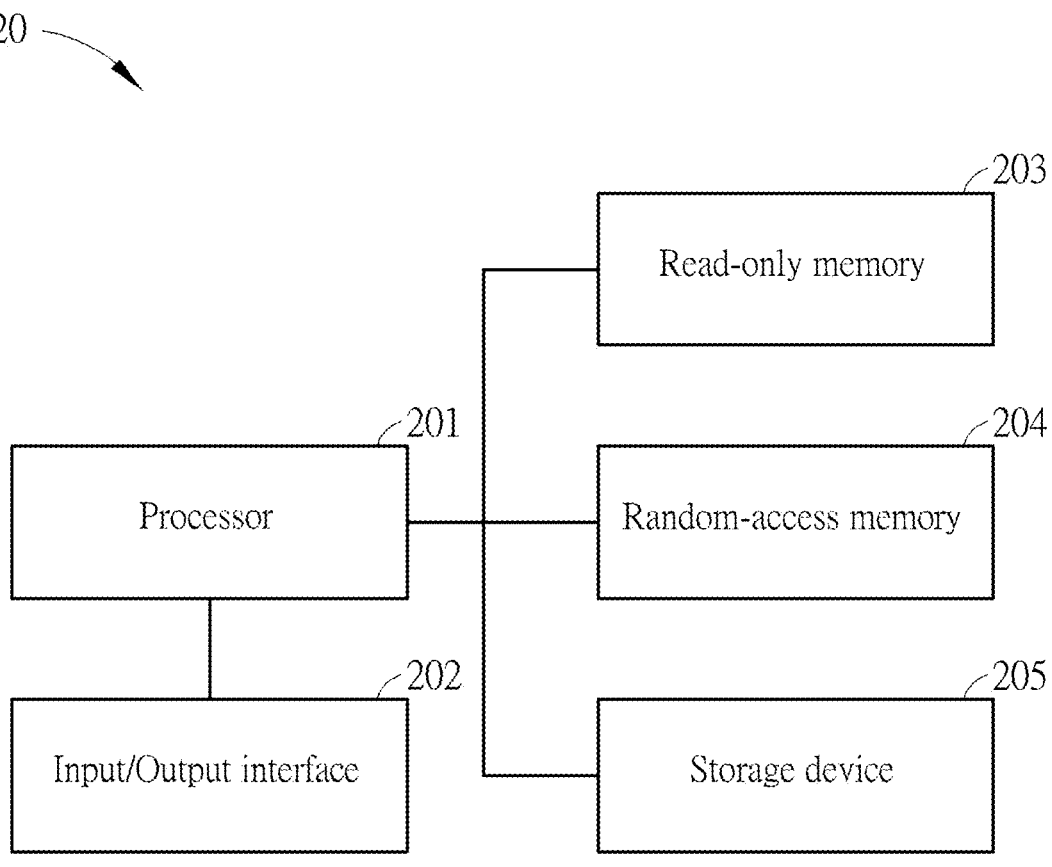
FIG. 3 is a schematic diagram of the computer according to at least one embodiment of the present disclosure.

FIG. 3 is a schematic diagram of the computer 20 according to at least one embodiments of the present disclosure. Here, the computer 20 may at least include, among other peripheral devices, a processor 201 configured to perform the computer-implemented method for predicting warping behavior of the product according to computer instructions, an input/output (I/O) interface 202 electrically coupled to the processor 201 for communicating with the injection-molding apparatus 10, and memories, which may include a read-only memory (ROM) 203, a random-access memory (RAM) 204 and a storage device 205. The ROM 203, the RAM 204 and the storage device 205 are communicatively coupled to the processor 201, and may be used to store data received from the injection-molding apparatus 10 and/or data generated by the processor 201 executing the method for predicting warping behavior of the product.

In the embodiments described herein, the method is conducted on a specimen of the product. The specimen used herein may be a prototype of the product, a sample portion of the product, the product itself, or any pieces of injection-molded materials of interest. Further, the warping behavior of the specimen may refer to the condition of the specimen being stored under a controlled atmosphere for a predetermined period of time, so as to allow any relaxation of the material in the specimen or post molding crystallization to take on effect in the warping behavior. Moreover, the specimen may be molded by material such as thermoplastics, thermosetting plastics, rubbers, elastomers, engineering plastics, biodegradable plastics, crystalline plastics, amorphous plastics, fiber plastics, fiber-free plastics, etc. In other embodiments, the specimen may be molded by at least one material selected from the group consisting of: polypropylene, polyethylene, high-density polyethylene, low-density polyethylene, polystyrene, polyvinyl chloride, acrylonitrile-butadiene-styrene copolymer resin, polyoxymethylene, polycarbonate, polyamine, thermoplastic elastomer, epoxy resin, phenolic resin, unsaturated polyester, silicone, nitrile rubber, polyethyleneimine, polyethylene terephthalate, polylactic acid, and polyhydroxyalkanoate, Polyetherketone, liquid crystal polymer, modified polyphenylene ether, polyphenylene sulfide, nylon resin, and acrylic resin.

Figure 4:
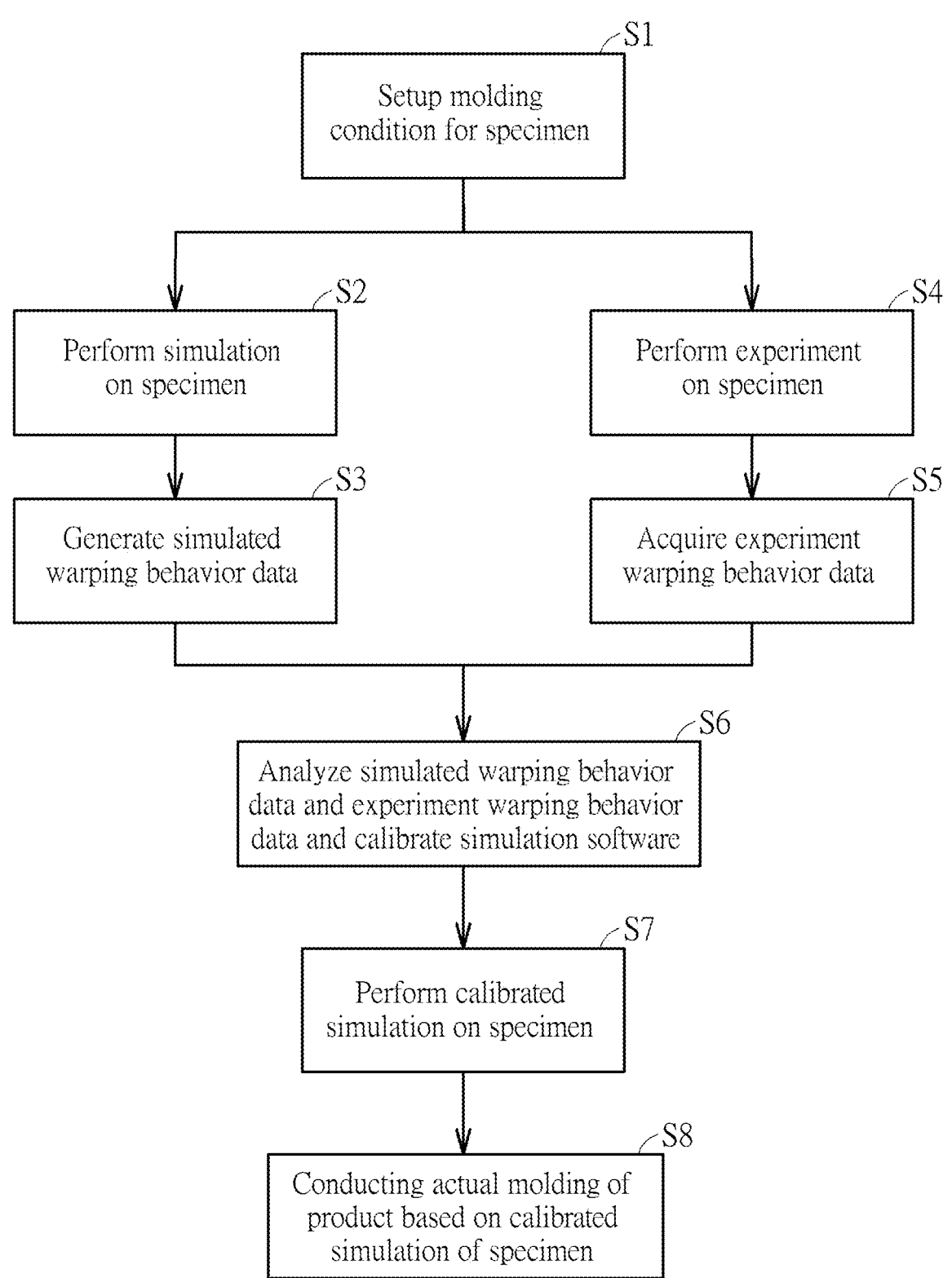
FIG. 4 is a flow diagram of the method for predicting the warping behavior according to at least one embodiment of the present disclosure.

FIG. 4 shows flow diagram of the method for predicting the warping behavior the product realized by the injection-molding apparatus 10 and the computer 20.

At step S1, molding condition (predetermined molding condition) of the specimen of the product may be setup for simulation and experiment purposes. In here, the predetermined molding condition may describe information such as a setting for material (such as, among other materials, nylon resin, polycarbonate, polypropylene and/or polystyrene) for molding the specimen, a setting for temperature of a mold for molding the specimen (such as, a value between 10 to 100 degrees Celsius), a setting for an estimated cooling time of the material (such as a value between 1 to 5 hours), a setting for molding thickness of the specimen (such as, a value between 1 to 5 mm), a setting for packing pressure for molding the specimen (such as a value between 30% to 130% of injection pressure of material by the injection-molding apparatus 10), and others. In other embodiments, the predetermined molding condition may include at least one selected from the group consisting of: a material for molding the specimen, an estimated cooling time of the material, a temperature of a mold for molding the specimen, an injection flow rate for injecting the material into the mold, an injection pressure for injecting the material into the mold, a packing pressure for molding the specimen, a packing time for molding the specimen, and a molding thickness of the specimen.

At step S2, the simulation software of the computer 20 may perform simulation of warping of specimen after injection-molding is completed. Moreover, FIG. 5 describes step S2 to include the detailed steps S201 and S202.

At step S201, the simulation software may establish a digital twin of the specimen. In some embodiments, the digital twin may be a three-dimensional model imported by the simulation software to resemble dimension of the specimen and/or material characteristics exhibited by the specimen in the real-world. For example, the digital twins may be established by importing the part and mold geometry into a meshing environment where a suitable discretization model, often using shell or solid elements, is created. After meshing, simulation may be carried out by defining material behavior using constitutive models that capture thermal, rheological, and mechanical properties under molding conditions.

At step S202, the simulation software may simulate warping behavior of the specimen using the digital twin according to operating condition of the injection-molding apparatus 10 and the predetermined molding condition set in step S1. To simulate warping behavior of the specimen, the simulation using the digital twin may include the sequential stages: a flow analysis to capture melt filling and packing dynamics, a thermal analysis to evaluate transient heat transfer and cooling behavior, and a mechanical analysis to compute part distortion. The temperature, pressure, and velocity derived from each sequence may serve as input conditions for subsequent sequences. Throughout the analysis, accurate coupling between thermal and mechanical responses may be obtained, and the residual stress distribution that ultimately drives warpage may be applied for prediction in the followings steps.

At step S3, the simulation software may generate simulated warping behavior data of the specimen under the predetermined molding condition according to simulation result of step S202 using the digital twin.

At step S4, an experiment may be conducted by performing injection-molding of the specimen using the injection-molding apparatus 10. Here, the experiment is performed based on the operating condition of the injection-molding apparatus 10 and the predetermined molding condition set in step S1, and the resulted specimen may act as control group for determining prediction accuracy of the present invention and basis for calibrating simulation performance of the simulation software.

At step S5, the injection-molding apparatus 10 may acquire experiment warping behavior data of the specimen from the experiment.

At step S6, the simulation software may analyze the simulated warping behavior data and the experiment warping behavior data of the specimen and calibrate the simulation performance of simulation software accordingly. Step S6 is performed based on the following findings regarding injection molding manufacturing:

1. Residual stresses developed during injection molding are among primary contributors to warpage and dimensional instability in products.

2. The residual stresses may be originated from thermal-induced mechanism and flow-induced mechanism, which is found to contribute to complex interactions of material behavior and process conditions that determine the final shape and mechanical property of the molded specimen.

3. Thermal-induced residual stress is triggered due to non-uniform cooling and pressure variation during solidification of material in the specimen. For example, in the glass transition region, the polymer may undergo rapid increase in rigidity. Therefore, as high temperature gradient across wall of the specimen appears, each segment of the specimen solidifies at a different time and creates differential shrinkage and internal stresses, and warpage and dimensional instability is formed.

4. The thermal-induced residual stress may also be contributed by local crystalline structure development in semi-crystalline polymers.

5. Flow-induced residual stress is triggered due to viscoelastic nature of the polymer melt during filling, packing and holding stages of the injection-molding process. For example, shear and elongational flow may result in said flow-induced residual stress, which may cause polymer chains, reinforcing fibers and crystalline domains to orient towards flow directions. The froze-in orientations of the above attributes may introduce significant anisotropy in the mechanical, thermal, and optical properties of the molded specimen, thus leading to directional shrinkage, birefringence, and long-term dimensional instability.

6. Due to the origin in macroscopic temperature gradients and volumetric changes, thermally-induced residual stresses are generally larger in magnitude than flow-induced residual stresses. However, the flow-induced residual stresses still have critical influence on warpage and dimensional instability in the molded specimen.

7. The flow-induced residual stresses is solved in this disclosure by advanced approach to analyze orientation effect and predicting its evolution using comprehensive theoretical models and isolating the contributions of flow-induced effects from other residual stress effects.

8. The characteristic effects that influence the warping of the product may include thermal, pressure, and crystalline effects derived from thermally-induced residual stress, flow-induced residual stress, and mechanical-induced residual stress, and the comprehensive theoretical models may be summarized as the following equation:

$$\varepsilon_{ij}^{total} = \varepsilon_{ij}^{M}\left(a^{M}\right) + \varepsilon_{ij}^{T}\left(a^{T}\right) + \varepsilon_{ij}^{P}\left(a^{P}\right) + \varepsilon_{ij}^{C}\left(a^{C}\right) + \varepsilon_{ij}^{F}\left(a^{F}\right), \qquad \text{equation (1)}$$

where it explains that the total strain $$\left(\varepsilon_{ij}^{total}\right)$$

of a warpage in principal coordinate system (noted by index notations i,j) may be decomposed into five characteristic effects (mechanical-induced effect $$\varepsilon_{ij}^{M},$$

thermal-induced effect $$\varepsilon_{ij}^{T},$$

pressure-induced effect $$\varepsilon_{ij}^{P},$$

crystalline-induced effect $$\varepsilon_{ij}^{C}$$

and flow-induced effect $$\varepsilon_{ij}^{F}),$$

and characteristic orientation effect ($a^{M}$, $a^{T}$, $a^{P}$, $a^{C}$, $a^{F}$) for each of the characteristic effect may be isolated from simulation of the characteristic effects to achieve the optimal simulation performance.

Moreover, FIG. 6 describes step S6 to include the detailed steps S601 to S606. The below listed equations are derived from equation (1), where distribution condition of characteristic orientation effect, if not necessarily required, may be omitted during analysis for simplicity.

At step S601, the simulation software may determine an experimental strain in a principal coordinate system from the experiment warping behavior data and a characteristic strain in the principal coordinate system from the simulated warping behavior data. Here, the experimental strain in the principal coordinate system may be expressed as the equation below:

$$\varepsilon_{ij}^{experiment}, ij \in 11, 22, \text{ or } 33, \qquad \text{equation (2)}$$

where i and j are index notations of the principal coordinate system; and the characteristic strain in the principal coordinate system may be expressed as the equation below:

$$\varepsilon_{ij}^{\Pi}, ij \in 11, 22, \text{ or } 33, \qquad \text{equation (3)}$$

where $\Pi$ represents index of a characteristic effect ($\Pi \in \{M, T, P, C, F\}$) imposing on the specimen during an injection-molding process.

In some embodiments, the characteristic strain may be used by the simulation software to formulate a simulated strain in the principal coordinate system, which may be expressed as the equation below:

$$\varepsilon_{ij}^{simulated} = \sum_{\Pi} \varepsilon_{ij}^{\Pi}, \; ij \in 11, 22, \text{ or } 33; \; \prod \in \{M, T, P, C, F\}. \quad \text{equation (4)}$$

Therefore, by simulating components (characteristic strains $$\varepsilon_{ij}^{\Pi})$$

of the simulated strain $$\varepsilon_{ij}^{simulated}$$

without influence by characteristic orientation effect, calibration relationships between the experimental strain $$\varepsilon_{ij}^{measured}$$

and characteristic strain $$\varepsilon_{ij}^{\Pi}$$

in the principal coordinate system may be discovered, and the simulation performance of the simulation software may be calibrated by making value of the simulated strain $$\varepsilon_{ij}^{simulated}$$

approaching the value of experimental strain $$\varepsilon_{ij}^{measured}$$

as close as possible according to the discovered calibration relationships.

In some embodiments, the index i and j of equation (2) and (3) may be used to express any one of the principal directions in the principal coordinate system: flow direction of an injection mold for molding the specimen (i and j are set as 1), cross direction of the flow direction (i and j are set as 2), and normal direction of the injection mold (i and j are set as 3). Further, the index $\Pi$ of the characteristic effect may correspond to at least one characteristic effect selected from the group consisting of mechanical-induced effect ($\Pi$ is set as "M"), thermal-induced effect ($\Pi$ is set as "T"), pressure-induced effect ($\Pi$ is set as "P"), crystalline-induced effect ($\Pi$ is set as "C") and flow-induced effect ($\Pi$ is set as "F").

Figure 7:
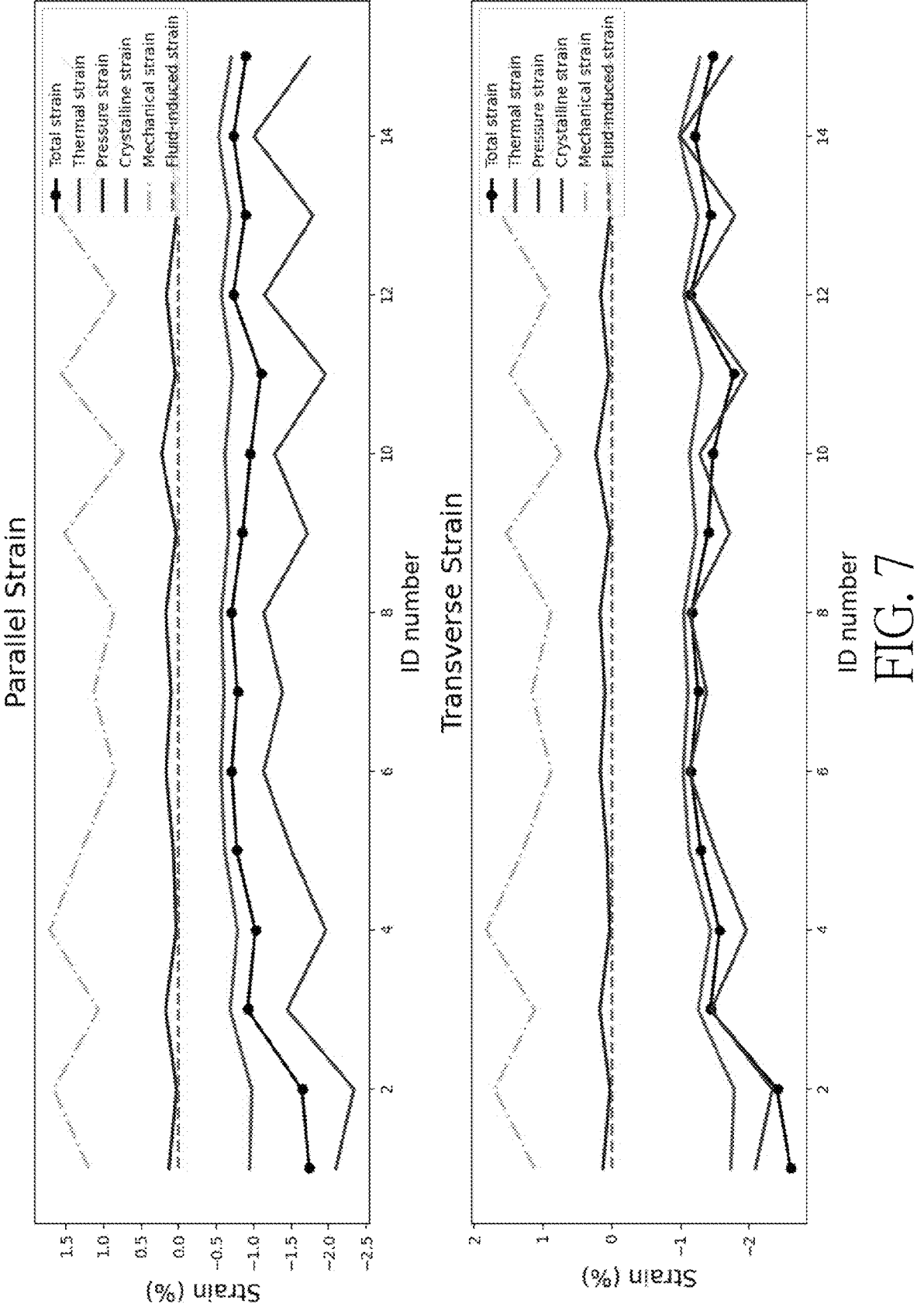
FIG. 7 is a schematic value chart of characteristic strains forming a simulated strain under an in-processing orienta-tion state according to at least one embodiment of the present disclosure.

FIG. 7 is an example of characteristic strains $$\varepsilon_{ij}^{\Pi},$$

while still under association with characteristic orientation effect, forming the simulated strain $$\varepsilon_{ij}^{simulated}$$

obtained through step S601, where only quantities on the flow direction and the cross direction of flow direction is shown. The top chart of FIG. 7 shows the simulated strain (black line, further noted as $$\varepsilon_{11}^{simulated})$$

at a flow direction (i and j are set as 1) of the specimen may be formed by a characteristic strain ($\Pi$ is set as "P", further noted as $$\varepsilon_{11}^{P})$$

under pressure-induced effect (blue line), a characteristic strain ($\Pi$ is set as "T", further noted as $$\varepsilon_{11}^{T})$$

under thermal-induced effect (red line), a characteristic strain ($\Pi$ is set as "M", further noted as $$\varepsilon_{11}^{M})$$

under mechanical-induced effect (light pink line), a characteristic strain ($\Pi$ is set as "C", further noted as $$\varepsilon_{11}^{C})$$

under crystalline-induced effect (purple line), and a characteristic strain (H is set as "F", further noted as $$\varepsilon_{11}^{F})$$

under flow-induced effect (bright pink line), where the vertical axis represents percentage (%) of warping caused by a specified strain on the specimen, and the horizontal axis represents identifier (ID) of predetermined molding condition relating to the warping caused by the specified strain. The bottom chart of FIG. 7 shows the simulated strain (black line, further noted as $$\varepsilon_{22}^{simulated})$$

11

12 at a cross direction (i and j are set as 2) of the flow direction of the specimen may be at least formed by a characteristic strain (Π is set as "P", further noted as $$\varepsilon_{22}^{P})$$

under pressure-induced effect (blue line), a characteristic strain (Π is set as "T", further noted as $$\varepsilon_{22}^{T})$$

under thermal-induced effect (red line), a characteristic strain (Π is set as "M", further noted as $$\varepsilon_{22}^{M})$$

under mechanical-induced effect (light pink line), a characteristic strain (Π is set as "C", further noted as $$\varepsilon_{22}^{C})$$

under crystalline-induced effect (purple line), and a characteristic strain (Π is set as "F", further noted as $$\varepsilon_{22}^{F})$$

under flow-induced effect (bright pink line).

At step S602, the simulation software may derive experimental stress and characteristic stress from experimental strain and characteristic strain, respectively. Here, a material constitutive equation may be used to derive the experimental stress and the characteristic stress, which may be expressed, according to Hook's Law, as the following equation:

for deriving experimental stress:

$$\sigma_{ij}^{experiment} = c_{ijkl}(a^{overall})\varepsilon_{kl}^{experiment}(a^{overall}), \qquad \text{equation (5)}$$

and for deriving characteristic stress:

$$\sigma_{ij}^{\Pi} = c_{ijkl}(a^{overall})\varepsilon_{kl}^{\Pi}(a^{\Pi}), \qquad \text{equation (6)}$$

where i, j, k, l represent index of principal directions in the principal coordinate system, $$\sigma_{ij}^{\Pi}$$

represents the experimental stress (Π experiment) or the characteristic stress (Π=P, T, M, C, or F), $$\varepsilon_{kl}^{\Pi}$$

represents the experimental strain (Π=experiment) or the characteristic strain (Π=P, T, M, C, or F), and $c_{ijkl}(a^{overall})$ represents a weakly-oriented overall stiffness coefficient tensor, $a^{overall}$ represents an overall effective orientation tensor under comprehensive influences of the warpage. Further, the weakly-oriented overall stiffness coefficient tensor $c_{ijkl}(a^{overall})$ in the principal coordinate system may be presented as orthotropic material property under the effect of the overall effective orientation tensor $a^{overall}$, which is related to nine engineering constants Young's moduli $E_x$, $E_y$, $E_z$, Poisson's ratios $v_{xy}$, $v_{yz}$, $v_{xz}$ and shear moduli $G_{xy}$, $G_{yz}$, $G_{xz}$.

In some embodiments, when deriving the characteristic stresses, overall effective orientation tensor $a^{overall}$ may be set as the mechanical-induced characteristic orientation tensor $a^M$, since it represents a comprehensive influences of all other characteristic orientation effects [$a^T$, $a^P$, $a^C$, $a^F$] being considered for simulation, which is an overall equivalent orientation tensor of the material in the solid state. In other embodiments, the overall effective orientation tensor $a^{overall}$ may be a highest value from the group of characteristic orientation tensors [$a^T$, $a^P$, $a^C$, $a^F$]. For example, if fiber orientation effect is the strongest for fiber-containing materials, the overall effective orientation tensor $a^{overall}$ may thus be set as the fiber orientation tensor. In further embodiments, the overall effective orientation tensor $a^{overall}$ may be a weighted average of the characteristic orientation tensors [$a^T$, $a^P$, $a^C$, $a^F$], where the weight of each characteristic orientation tensor is expressed as $$[|\varepsilon_{ij}^T|, |\varepsilon_{ij}^P|, |\varepsilon_{ij}^C|, |\varepsilon_{ij}^F|].$$

On the other hand, when deriving the experimental stress, only the overall effective orientation tensor $a^{overall}$ is included since the experimental stress is only related to the overall effective orientation effect.

Further, in continuous to the equations (2) and (4) described above, the experimental strain and the simulated strain in the principal coordinate system may be converted by the material constitutive equation to derive the experimental stress and simulated stress written as below:

$$\sigma_{ij}^{experiment} \Leftrightarrow \sigma_{ij}^{simulated} = \sum_{\Pi} \sigma_{ij}^{\Pi}, \qquad \text{equation (7)}$$

$$ij \in 11, 22 \text{ or } 33; \Pi \in \{M, T, P, C, F\},$$

where $$\sigma_{ij}^{experiment}$$

represents the experimental stress, $$\sigma_{ij}^{simulated}$$

represents the simulated stress, and $$\sigma_{ij}^{\Pi}$$

represents the characteristic stress forming the simulated stress.

At step S603, the simulation software may: convert the experimental stress from an in-processing orientation state to a fully-aligned orientation state in a pseudo coordinate system to obtain an orientation-calibrated experimental stress at a transverse direction of the specimen and an orientation-calibrated experimental stress at a parallel direction of the specimen; and convert the characteristic stress to the fully-aligned orientation state to obtain an orientation-calibrated characteristic stress at the transverse direction and an orientation-calibrated characteristic stress at the parallel direction, such that material anisotropy caused by characteristic orientation effect such as fiber orientation, molecular orientation and/or crystal orientation in the specimen may be isolated from the characteristic effect during the following analysis. Here, as explained in FIG. 8, the conversion to the fully-aligned orientation state may transform the physical quantity observed under the weakly-aligned in-processing orientation state (left image of FIG. 8) into an equivalent quantity on a transverse direction and a parallel direction under a fully-aligned orientation state (right image of FIG. 8). This transformation enables decoupling of characteristic orientation effect caused by material anisotropy in the specimen and allows for regression and calibration of the simulation software in a consistent and orientation-independent manner. Moreover, the conversion to the fully-aligned orientation state may be expressed as:

for obtaining the orientation-calibrated experimental stress:

$$\sigma_{IJ}^{experiment} = A_{IJkl}(a^{overall})\sigma_{kl}^{experiment}, \qquad \text{equation (8)}$$

and for obtaining the orientation-calibrated characteristic stress:

$$\sigma_{IJ}^{\Pi} = A_{IJkl}(a^{\Pi})\sigma_{kl}^{\Pi}, \qquad \text{equation (9)}$$

where I, J, K, L represent index of principal directions in a pseudo principal coordinate system in fully-aligned orientation state, $\sigma_{IJ}$ represent the orientation-calibrated experimental stress ($\Pi$=experiment) or the orientation-calibrated characteristic stress ($\Pi$=P, T, M, C, or F) on a transverse (IJ=$\perp$) or parallel (IJ=$\parallel$) direction in the fully-aligned orientation state in the pseudo coordinate system, and the function $A_{IJKL}(a^{\Pi})$ or $A_{IJKL}(a^{overall})$ represents a simplified conversion matrix for converting the stress tensors from the in-processing orientation state to the fully-aligned orientation state, which may be related to construction means of the closure approximation method for fourth-order tensors, and may include, but not limited to, the operation of linear, quadratic, hybrid, orthotropic and invariant based optimal fitting (IBOF) approximation methods. That is, the equation (7) in step S602 may be converted in step S603 to express as:

$$\sigma_{IJ}^{experiment} \Leftrightarrow \sigma_{IJ}^{simulated} = \sum_{\Pi} \sigma_{IJ}^{\Pi}, \qquad \text{equation (10)}$$

$$IJ \in \perp \text{ or } \parallel; \Pi \in \{M, T, P, C, F\},$$

based on the function $A_{IJKL}(a^{overall})$ and $A_{IJKL}(a^{\Pi})$.

At step S604, the simulation software may: determine an orientation-calibrated experimental strain at the transverse direction and an orientation-calibrated experimental strain at the parallel direction according to the orientation-calibrated experimental stress at the transverse direction and the orientation-calibrated experimental stress at the parallel direction, respectively; and determine a orientation-calibrated characteristic strain at the transverse direction and an orientation-calibrated characteristic strain at the parallel direction according to the orientation-calibrated characteristic stress at the transverse direction and the orientation-calibrated characteristic stress at the parallel direction, respectively. Here, a fully-oriented material constitutive equation may be used to derive the orientation-calibrated experimental strain at the transverse direction, the orientation-calibrated experimental strain at the parallel direction, the orientation-calibrated characteristic strain at the transverse direction, and the orientation-calibrated characteristic strain at the parallel direction, which may be expressed, according to the Hook's Law, as the following equation:

for determining orientation-calibrated experimental strain:

$$\varepsilon_{IJ}^{exp} = s_{IJKL}\sigma_{KL}^{exp}, IJ \in \perp \text{ or } \parallel, \qquad \text{equation (11)}$$

for determining orientation-calibrated characteristic strain:

$$\varepsilon_{IJ}^{\Pi} = s_{IJKL}\sigma_{KL}^{\Pi}, IJ \in \perp \text{ or } \parallel; \Pi \in \{M, T, P, C, F\} \qquad \text{equation (12)}$$

where $s_{IJKL}$ represents a fully-aligned overall compliance coefficient tensor. Therefore, since the fully-aligned orientation state in the pseudo coordinate system only has a parallel direction and a transverse direction, the fully-aligned overall compliance coefficient tensor $s_{IJKL}$ in the pseudo coordinate system may be presented as transversely isotropic material property, which is related to only five engineering constants Young's moduli $E_{\parallel}$, $E_{\perp}$, Poisson's ratios $v_{\parallel\perp}$, $v_{\perp\perp}$ and shear moduli $G_{\parallel\perp}$ and is beneficial in simplifying simulation load of the system.

Moreover, the relationship between the orientation-calibrated experimental strain at the transverse direction, the orientation-calibrated experimental strain at the parallel direction, the orientation-calibrated characteristic strain at the transverse direction, and the orientation-calibrated characteristic strain at the parallel direction, after application of the fully-oriented material constitutive equation, may be written as the equation below:

$$\begin{cases} \varepsilon_{\parallel}^{experiment} \\ \varepsilon_{\parallel}^{experiment} \end{cases} \Leftrightarrow \begin{cases} \varepsilon_{\parallel}^{experiment} = \sum_{\Pi} \varepsilon_{\parallel}^{\Pi} \\ \varepsilon_{\parallel}^{simulated} = \sum_{\Pi} \varepsilon_{\perp}^{\Pi} \end{cases}, \qquad \text{equation (13)}$$

15

Figure 9:
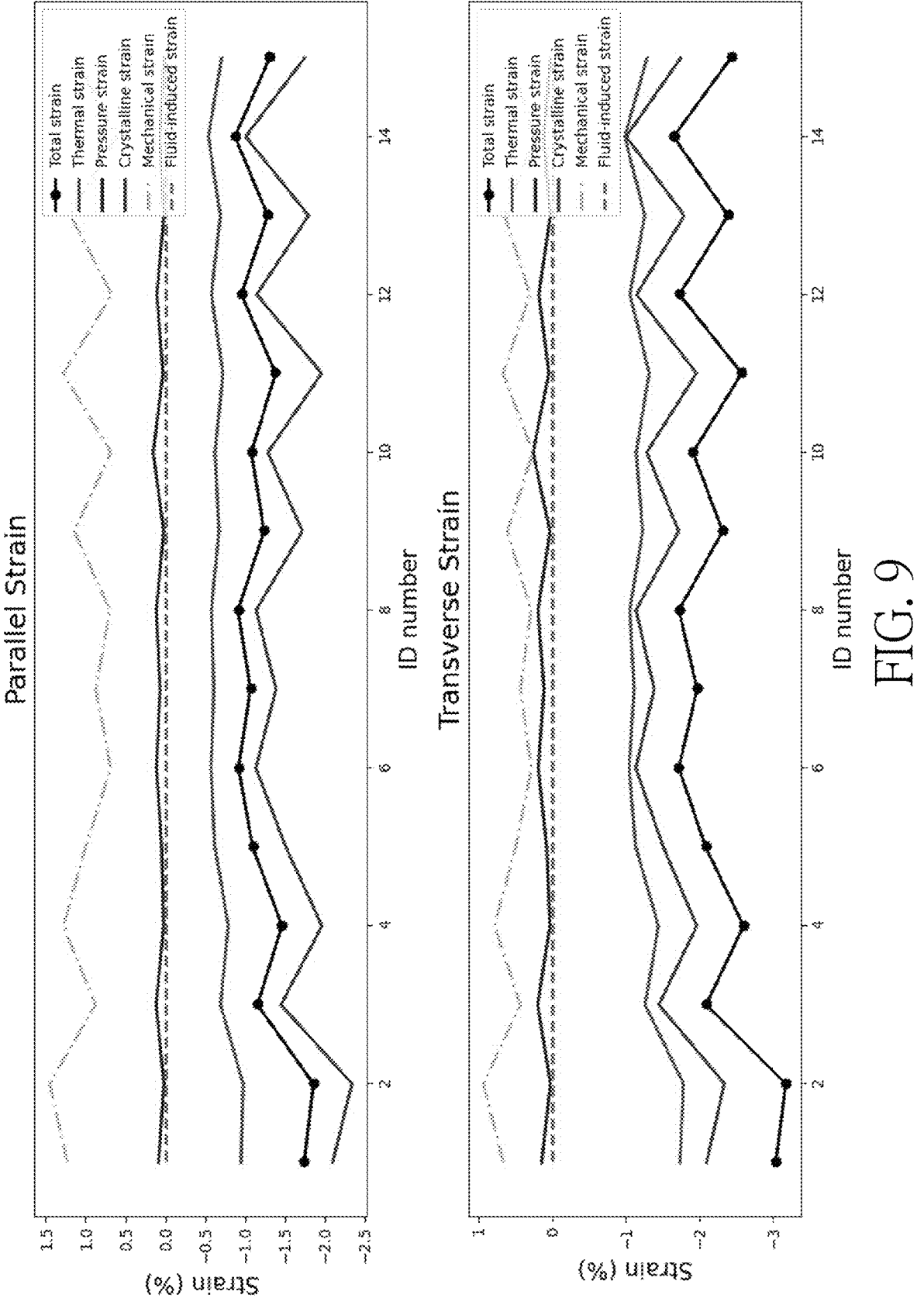
FIG. 9 is a schematic value chart of orientation-calibrated characteristic strains at the transverse direction forming an orientation-calibrated simulated strain at the transverse direction and orientation-calibrated characteristic strains at the parallel direction forming the orientation-calibrated simulated strain at the parallel direction.

16 where forming the orientation-calibrated simulated strain $$\varepsilon_{\parallel}^{experiment}$$

$$\varepsilon_{\perp}^{simulated}$$

represents the orientation-calibrated experimental strain at the parallel direction, obtained through step S604. The top chart of FIG. 9 shows the orientation-calibrated simulated strain $$\varepsilon_{\perp}^{experiment}$$

$$\varepsilon_{\parallel}^{simulated}$$

represents the orientation-calibrated experimental strain at the transverse direction, (black line) at the parallel direction of the specimen may be formed by an orientation-calibrated characteristic strain (Π is set as "P", further noted as $$\varepsilon_{\parallel}^{simulated}$$

$$\varepsilon_{\parallel}^{P})$$

represents an orientation-calibrated simulated strain at the parallel direction, under pressure-induced effect (blue line), an orientation-calibrated characteristic strain (Π is set as "T", further noted as $$\varepsilon_{\perp}^{simulated}$$

$$\varepsilon_{\parallel}^{T})$$

represents an orientation-calibrated simulated strain at the transverse direction, under thermal-induced effect (red line), an orientation-calibrated characteristic strain (Π is set as "M", further noted as $$\varepsilon_{\parallel}^{\Pi}$$

$$\varepsilon_{\parallel}^{M})$$

represents the orientation-calibrated characteristic strain forming the orientation-calibrated simulated strain at the parallel direction, and under mechanical-induced effect (light pink line), an orientation-calibrated characteristic strain (Π is set as "C", further noted as $$\varepsilon_{\perp}^{\Pi}$$

$$\varepsilon_{\parallel}^{C})$$

represents the orientation-calibrated characteristic strain forming the orientation-calibrated simulated strain at the transverse direction.

under crystalline-induced effect (purple line), and an orientation-calibrated characteristic strain (Π is set as "F", further noted as FIG. 9 is an example of orientation-calibrated characteristic strain $$\varepsilon_{\parallel}^{F})$$

$$\varepsilon_{\parallel}^{\Pi}$$

under flow-induced effect (bright pink line), where the vertical axis represents percentage (%) of warping caused by a specified parallel strain on the specimen, and the horizontal axis represents identifier (ID) of predetermined molding condition relating to the warping caused by the specified parallel strain. The bottom chart of FIG. 9 shows the orientation-calibrated simulated strain forming the orientation-calibrated simulated strain $$\varepsilon_{\parallel}^{simulated}$$

and orientation-calibrated characteristic strain $$\varepsilon_{\perp}^{simulated}$$

$$\varepsilon_{\perp}^{\Pi}$$

(black line) at the transverse direction of the specimen may be formed by an orientation-calibrated characteristic strain (Π is set as "P", further noted as $$\varepsilon_{\perp}^{P})$$

under pressure-induced effect (blue line), an orientation-calibrated characteristic strain ($\Pi$ is set as "T", further noted as $$\varepsilon_{\perp}^{T})$$

under thermal-induced effect (red line), an orientation-calibrated characteristic strain ($\Pi$ is set as "M", further noted as $$\varepsilon_{\perp}^{M})$$

under mechanical-induced effect (light pink line), an orientation-calibrated characteristic strain ($\Pi$ is set as "C", further noted as $$\varepsilon_{\perp}^{C})$$

under crystalline-induced effect (purple line), and an orientation-calibrated characteristic strain ($\Pi$ is set as "F", further noted as $$\varepsilon_{\perp}^{F})$$

under flow-induced effect (bright pink line).

At step S605, the simulation software may perform a regression analysis to obtain a conversion relationship between the orientation-calibrated experimental strain at the parallel direction and the orientation-calibrated characteristic strain at the parallel direction and between the orientation-calibrated experimental strain at the transverse direction and the orientation-calibrated characteristic strain at the transverse direction. Here, the regression analysis may be realized through any one of the following: linear regression, polynomial regression, ridge regression, Lasso regression, logistic regression, Bayesian regression, decision tree regression, neural network regression, etc. Further, the regression analysis may be based on a hypothesis expressed as the following:

$$\varepsilon_{\Gamma}^{experiment} = \sum_{\Pi} R_{\Gamma}^{\Pi} \varepsilon_{\Gamma}^{\Pi} + r_{\Gamma}, \qquad \text{equation (14)}$$

where $\Gamma$ represents an index for transverse direction (noted as "$\perp$") or parallel direction (noted as "$\|$") of the specimen, $R_{\Gamma\Pi}$ represents a regression parameter for calibrating the orientation-calibrated characteristic strain at the transverse direction or the orientation-calibrated characteristic strain at the parallel direction, and $r_{\Gamma}$ represents a residual in arbitrary real number. Moreover, after influence of the residuals $r_{\Gamma}$ is eliminated, a calibrated-simulated warping behavior data corresponding to the original simulated warping behavior data may be obtained in the expression below:

$$\varepsilon_{\Gamma}^{calibrated} = \sum_{\Pi} R_{\Gamma}^{\Pi} \varepsilon_{\Gamma}^{\Pi}, \qquad \text{equation (15)}$$

where $$\varepsilon_{\Gamma}^{calibrated}$$

represents a calibrated simulated strain at a parallel direction ($\Gamma$ is set as "$\|$") or a calibrated-simulated strain at a transverse direction ($\Gamma$ is set as "$\perp$").

At step S606, the simulation software may utilize the conversion relationship to calibrate its simulation performance. That is, for example, when the simulation software originally obtained orientation-calibrated characteristic strains $$\varepsilon_{\|}^{M}, \varepsilon_{\|}^{T}, \varepsilon_{\|}^{P}, \varepsilon_{\|}^{C}, \text{and } \varepsilon_{\|}^{F}$$

and orientation-calibrated characteristic strains $$\varepsilon_{\perp}^{M}, \varepsilon_{\perp}^{T}, \varepsilon_{\perp}^{P}, \varepsilon_{\perp}^{C}, \text{and } \varepsilon_{\perp}^{F}$$

from step S604, the quantities will then be converted by the conversion relationship to obtain a calibrated-simulated strain $$\varepsilon_{\|}^{calibrated}$$

and a calibrated-simulated strain $$\varepsilon_{\perp}^{calibrated}$$

(collectively noted as "calibrated-simulated warping behavior data") at step S606, which may express, in accordance with equation (15), as below:

$$\begin{cases} \varepsilon_{\|}^{calibrated} = R_{\|}^{M}\varepsilon_{\|}^{M} + R_{\|}^{T}\varepsilon_{\|}^{T} + R_{\|}^{P}\varepsilon_{\|}^{P} + R_{\|}^{C}\varepsilon_{\|}^{C} + R_{\|}^{F}\varepsilon_{\|}^{F} \\ \varepsilon_{\perp}^{calibrated} = R_{\perp}^{M}\varepsilon_{\perp}^{M} + R_{\perp}^{T}\varepsilon_{\perp}^{T} + R_{\perp}^{P}\varepsilon_{\perp}^{P} + R_{\perp}^{C}\varepsilon_{\perp}^{C} + R_{\perp}^{F}\varepsilon_{\perp}^{F} \end{cases} \quad \text{equation (16)}$$

where $$R_{\|}^{M}$$

and $$R_{\perp}^{M}$$

may be a regression parameter corresponding to a calibrated mechanical property of the material of the specimen contributing to the calibrated-simulated strain $$\varepsilon_{\parallel}^{calibrated}$$

and/or the calibrated-simulated strain $$\varepsilon_{\perp}^{calibrated}$$

under the predetermined molding condition, $$R_{\parallel}^{T}$$

and $$R_{\perp}^{T}$$

may be a regression parameter corresponding to a calibrated thermal property of the material of the specimen contributing to the calibrated-simulated strain $$\varepsilon_{\parallel}^{calibrated}$$

and/or the calibrated-simulated strain $$\varepsilon_{\perp}^{calibrated}$$

under the predetermined molding condition, $$R_{\parallel}^{P} \text{ and } R_{\perp}^{P}$$

may be a regression parameter corresponding to a calibrated pressure distribution of the material of the specimen contributing to the calibrated-simulated strain $$\varepsilon_{\parallel}^{calibrated}$$

and/or the calibrated-simulated strain $$\varepsilon_{\perp}^{calibrated}$$

under the predetermined molding condition, $$R_{\parallel}^{C} \text{ and } R_{\perp}^{C}$$

may be a regression parameter corresponding to a calibrated crystalline shrinkage of the material of the specimen contributing to the calibrated-simulated strain $$\varepsilon_{\parallel}^{calibrated}$$

and/or the calibrated-simulated strain $$\varepsilon_{\perp}^{calibrated}$$

under the predetermined molding condition, and $$R_{\parallel}^{F} \text{ and } R_{\perp}^{F}$$

may be a regression parameter corresponding to a calibrated flow-induced residual stress of the material of the specimen contributing to the calibrated-simulated strain $$\varepsilon_{\parallel}^{calibrated}$$

and/or the calibrated-simulated strain $$\varepsilon_{\perp}^{calibrated}$$

under the predetermined molding condition.

Figure 10:
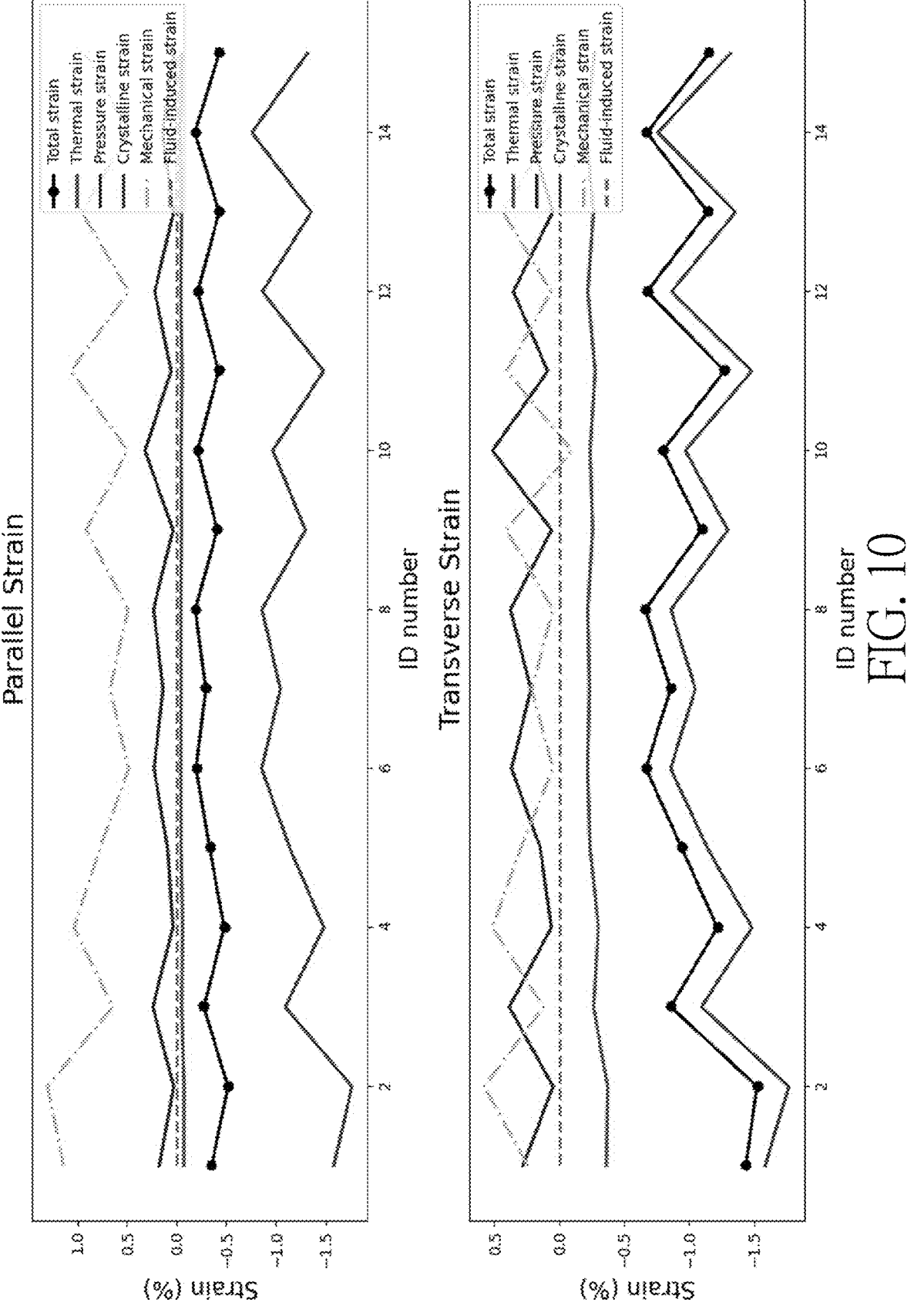
FIG. 10 is a schematic value chart of orientation-cali-brated characteristic strains at the transverse direction form-ing an orientation-calibrated simulated strain at the trans-verse direction and orientation-calibrated characteristic strains at the parallel direction forming the orientation-calibrated simulated strain at the parallel direction using a regression parameter obtained through regression analysis.

FIG. 10 is an example of orientation-calibrated characteristic strain $$\varepsilon_{\parallel}^{\Pi}$$

forming the calibrated-simulated strain $$\varepsilon_{\parallel}^{calibrated}$$

and orientation-calibrated characteristic strain $$\varepsilon_{\perp}^{\Pi}$$

forming the calibrated-simulated strain $$\varepsilon_{\perp}^{calibrated}$$

obtained through calibration using the regression parameter through step S605 and S606. The top chart of FIG. 10 shows the calibrated-simulated strain $$\varepsilon_{\parallel}^{calibrated}$$

(black line) at the parallel direction of the specimen may be formed by an orientation-calibrated characteristic strain ($\Pi$ is set as "P", further noted as $$\varepsilon_{\parallel}^{P})$$

under pressure-induced effect (blue line), an orientation-calibrated characteristic strain ($\Pi$ is set as "T", further noted as $$\varepsilon_{\parallel}^{T})$$

under thermal-induced effect (red line), an orientation-calibrated characteristic strain ($\Pi$ is set as "M", further noted as $$\varepsilon_{\parallel}^{M})$$

under mechanical-induced effect (light pink line), an orientation-calibrated characteristic strain ($\Pi$ is set as "C", further noted as $$\varepsilon_{\parallel}^{C})$$

under crystalline-induced effect (purple line), and an orientation-calibrated characteristic strain ($\Pi$ is set as "F", further noted as $$\varepsilon_{\parallel}^{F})$$

under flow-induced effect (bright pink line), where the vertical axis represents percentage (%) of warping caused by a specified parallel strain on the specimen, and the horizontal axis represents identifier (ID) of predetermined molding condition relating to the warping caused by the specified parallel strain. The bottom chart of FIG. 10 shows the calibrated-simulated strain $$\varepsilon_{\perp}^{calibrated}$$

(black line) at the transverse direction of the specimen may be formed by a orientation-calibrated characteristic strain ($\Pi$ is set as "P", further noted as $$\varepsilon_{\perp}^{P})$$

under pressure-induced effect (blue line), an orientation-calibrated characteristic strain ($\Pi$ is set as "T", further noted as $$\varepsilon_{\perp}^{T})$$

under thermal-induced effect (red line), an orientation-calibrated characteristic strain ($\Pi$ is set as "M", further noted as $$\varepsilon_{\perp}^{M})$$

under mechanical-induced effect (light pink line), an orientation-calibrated characteristic strain ($\Pi$ is set as "C", further noted as $$\varepsilon_{\perp}^{C})$$

under crystalline-induced effect (purple line), and an orientation-calibrated characteristic strain ($\Pi$ is set as "F", further noted as $$\varepsilon_{\perp}^{F})$$

under flow-induced effect (bright pink line).

At step S7, the simulation software may perform calibrated simulation on the specimen. Here, the calibrated simulation may refer to generating a calibrated-simulated warping behavior data (including the calibrated-simulated strain at the transverse direction and the calibrated-simulated strain at the parallel direction) of the specimen under the predetermined molding condition previously set in step S2 and S3 using the digital twin according to the conversion relationship; and/or generating additional-simulated warping behavior data of the specimen under a given molding condition (different than the predetermined molding condition) using the digital twin according to the conversion relationship.

Figure 11:
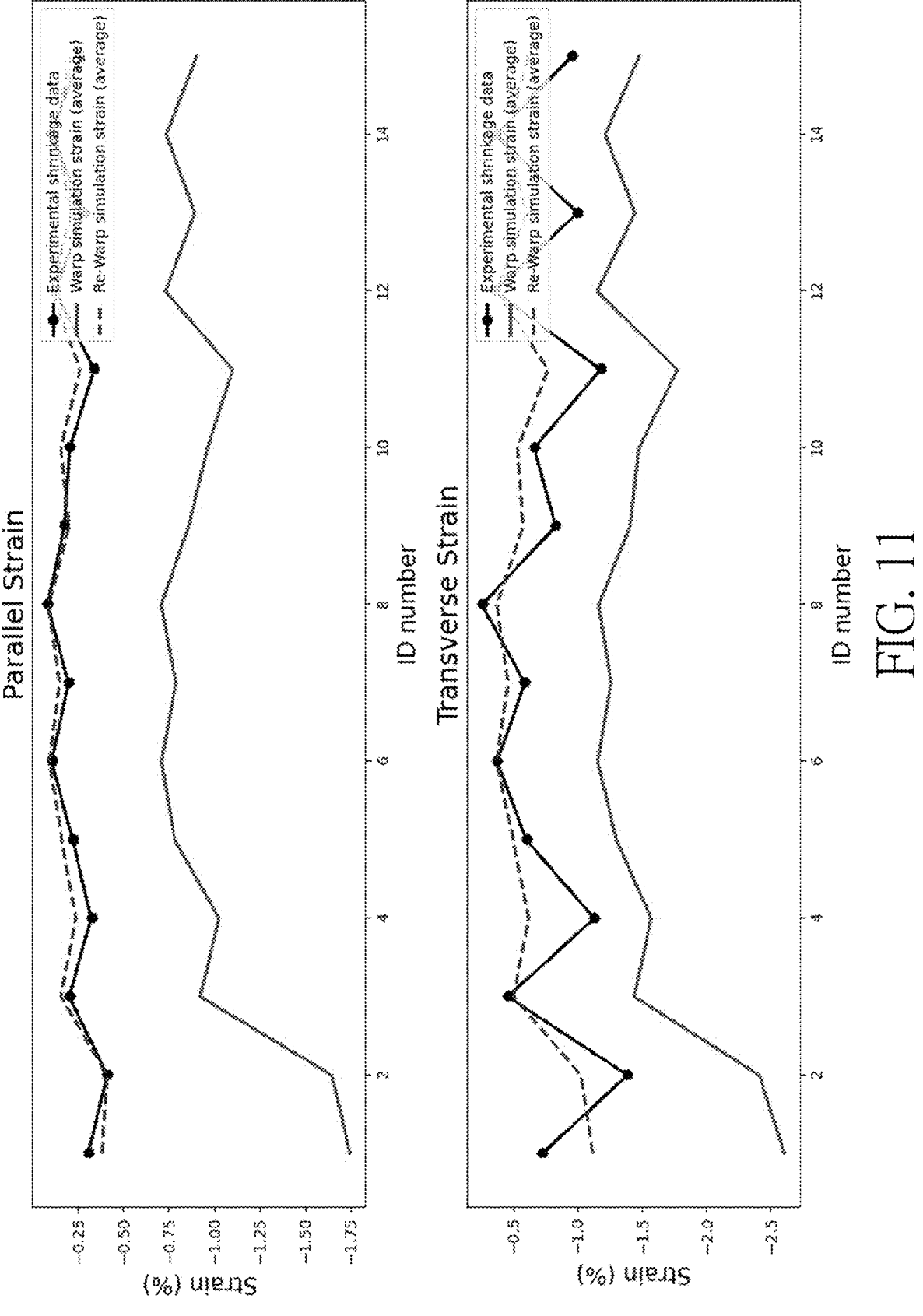
FIG. 11 is a schematic value chart of comparison between the experiment warping behavior data, the simulated warp-ing behavior data and the calibrated-simulated warping behavior data of a specimen.

FIG. 11 shows embodiments where calibrated simulation is conducted on the specimen using the predetermined molding condition previously set in step S2 and S3, where experiment warping behavior data of the specimen is included to evaluate the calibrated simulation performance.

FIG. 11 is an example of comparison between the experiment warping behavior data, the simulated warping behavior data and the calibrated-simulated warping behavior data of a specimen made with polycaprolactam under a same predetermined molding condition after completion of step S606. The top image of FIG. 11 shows that the calibrated-simulated strain (purple line) at the transverse direction, when compared with simulated strain (red line), is similar to (aligned with) the experimental strain (black line). The bottom image of FIG. 11 shows that the calibrated-simulated strain (purple line) at the parallel direction, when compared with simulated strain (red line), is similar to (aligned with) the experimental strain (black line). Therefore, it is clear that the simulation software has a more accurate simulation performance after calibration performed in steps S601 to S606.

Figure 12A:
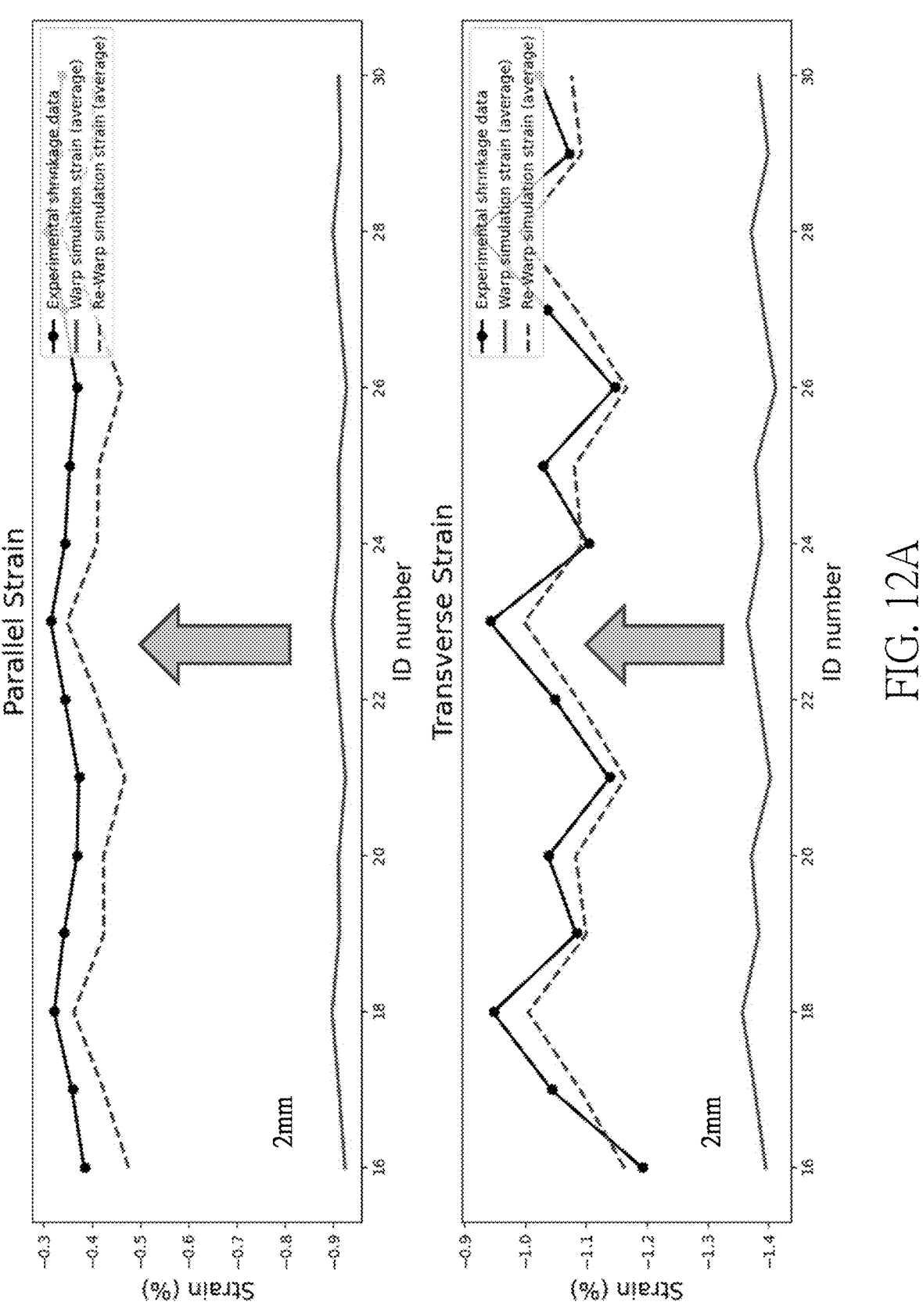
FIG. 12A is a schematic value chart of comparison between experiment warping behavior data, the simulated warping behavior data, and the calibrated-simulated warping behavior data of a new specimen.
Figure 12B:
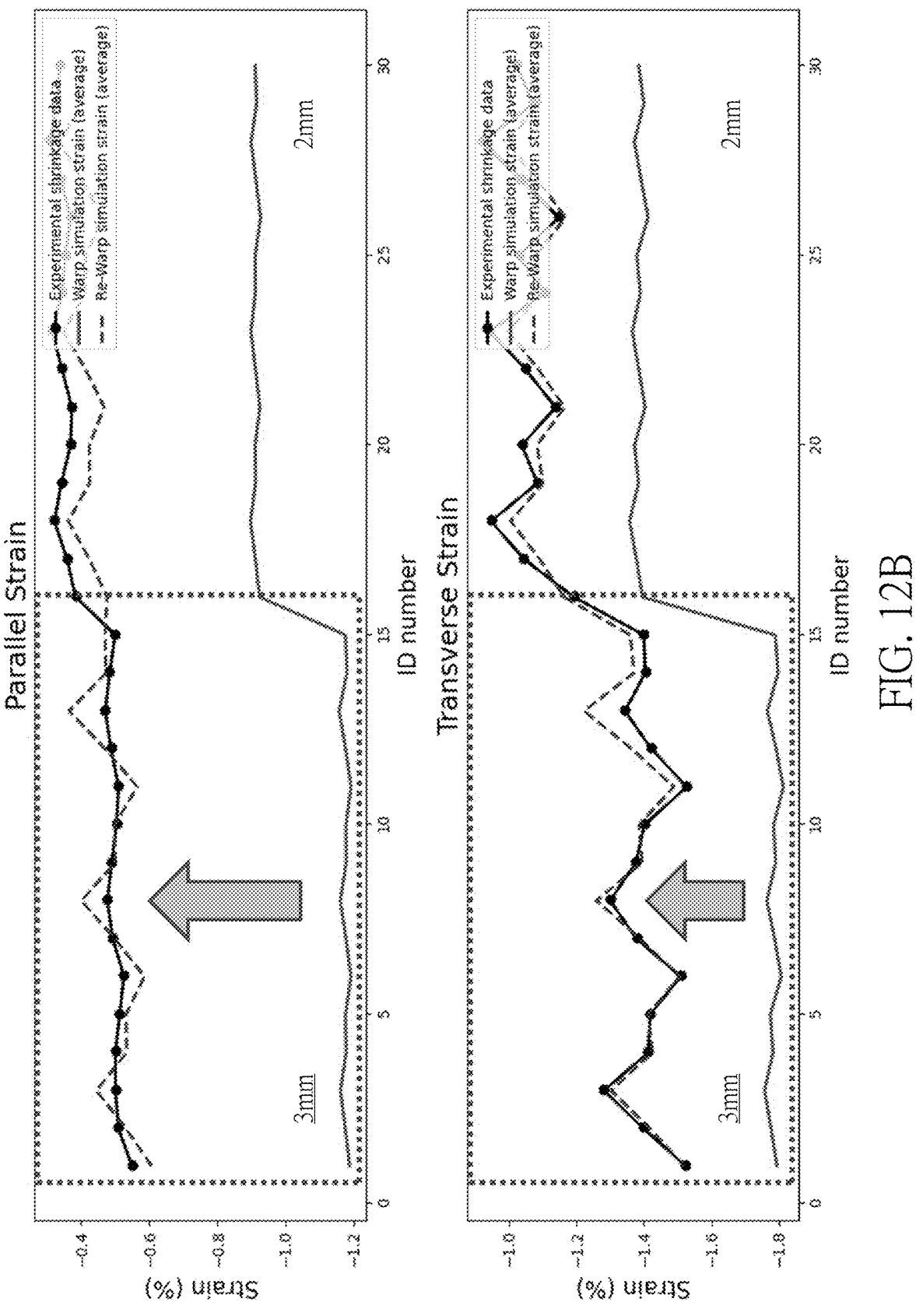
FIG. 12B is a schematic value chart of comparison between experiment warping behavior data, the simulated warping behavior data, the calibrated-simulated warping behavior data and the additional-simulated warping behav-ior data of a new specimen.

FIGS. 12A and 12B shows embodiments where calibrated simulation is conducted on the specimen using the given molding condition different than the predetermined molding condition, where the given molding condition defines a second molding thickness of the specimen different from the first molding thickness of the specimen using the predetermined molding condition, where experiment warping behavior data of the specimen is included to evaluate the calibrated simulation performance.

FIGS. 12A and 12B show an example of comparison between experiment warping behavior data, the simulated warping behavior data, the calibrated-simulated warping behavior data and the additional-simulated warping behavior data of a specimen made with fiber nylon. In here, the value chart marked with 2 mm shows the experiment warping behavior data, the simulated warping behavior data and the calibrated-simulated warping behavior data of a specimen produced under the predetermined molding condition (specimen thickness being 2 mm), while the value chart marked with 3 mm shows the additional-simulated warping behavior data of the specimen under the given molding condition (specimen thickness being 3 mm). Therefore, it is clear that even if calibration at step S601 to S606 is only performed based on the predetermined molding condition (specimen thickness being 2 mm), the obtained conversion relationship from step S606 is still applicable to calibrate simulation of the specimen under other molding conditions while maintaining the additional-simulated warping behavior data aligning to the experiment warping behavior data (in FIGS. 12A and 12B, the purple line representing the calibrated-simulated warping behavior data and the additional-simulated warping behavior data is similar to (aligned with) the black line representing the experiment warping behavior data, while the red line representing the simulated warping behavior data is much off from the black line).

At step S8, the injection-molding apparatus 10 may conduct an actual molding of the product according to the calibrated-simulated warping behavior data of the specimen and/or a given molding condition. From here, since possible warping behavior of the product is already simulated by the simulation software, a technician operating the injection-molding apparatus 10 may adjust the operation conditions of the injection-molding apparatus to achieve better quality of the injection-molded product.

Based on the above, the method for predicting warping behavior of the present disclosure may simulate warping behavior of a specimen based on independent characteristic effects imposing on the specimen, perform simulation in a consistent and orientation-independent manner, and enable calibration of simulation performance in a flexible manner. Therefore, prediction of warping behavior may be achieved with high accuracy and low resource requirement.

Those skilled in the art will readily observe that numerous modifications and alterations of the embodiments may be made while retaining the teachings of the present disclosure. Accordingly, the above disclosure should be construed as limited only by the metes and bounds of the appended claims.

What is claimed is:

1. A system for predicting warping behavior in a product, comprising:

an injection-molding apparatus configured to carry out a molding process of a product and monitor operating conditions during molding of the product;

and a computer coupled with the injection-molding apparatus, and carrying a simulation software, wherein the simulation software is configured for, when being executed by the computer, simulating the molding conditions of the product according to the operating conditions of the injection-molding apparatus, predetermined molding conditions, and/or given molding conditions;

wherein simulating the molding conditions comprises:

acquiring, via the injection-molding apparatus, experiment warping behavior data of a specimen of the product;

generating simulated warping behavior data of the specimen via the simulation software;

determining an experimental strain and a characteristic strain from the experiment warping behavior data of the specimen of the product and the simulated warping behavior data of the specimen, respectively, in an in-processing state, of a principal coordinate system;

deriving an experimental stress and a characteristic stress from the experimental strain and the characteristic strain, respectively, in the in-processing state;

converting the experimental stress and the characteristic stress from the in-processing state to a fully-aligned orientation state to obtain orientation-calibrated stresses at a transverse direction and a parallel direction of a pseudo coordinate system;

generating additional-simulated warping behavior data of the specimen under a given molding condition based on the conversion relationship derived from the orientation-calibrated stresses; and wherein the injection-molding apparatus is further configured to conduct an actual molding of the product according to the additional-simulated warping behavior data.

2. The system of claim 1, wherein the simulation software simulating the molding conditions of the product further comprises:

generating, via the simulation software, additional-simulated warping behavior data of the specimen under a given molding condition according to the conversion relationship; and conducting, via the injection-molding apparatus, an actual molding of the product according to the given molding condition, wherein a first molding thickness of the specimen described in the predetermined molding condition and a second molding thickness of the specimen described in the given molding condition are different from each other.

3. The system of claim 1, wherein the predetermined molding condition comprises at least one selected from the group consisting of a material for molding the specimen, an estimated cooling time of the material, a temperature of a mold for molding the specimen, an injection flow rate for injecting the material into the mold, an injection pressure for injecting the material into the mold, a packing pressure for molding the specimen, a packing time for molding the specimen, and a molding thickness of the specimen.

4. The system of claim 1, wherein the principal coordinate system defines at least one principal directions selected from the group consisting of: a flow direction of an injection mold for molding the specimen, a cross direction of the flow direction, and a normal direction of the injection mold.

5. The system of claim 1, wherein:

the characteristic strain and the characteristic stress correspond to at least one characteristic effect selected from the group consisting of mechanical-induced effect, thermal-induced effect, pressure-induced effect, crystalline-induced effect and flow-induced effect; and the at least one characteristic effect is imposed on the specimen during an injection-molding process.

6. The system of claim 1, wherein deriving, via the simulation software, the experimental stress in the principal coordinate system from the experimental strain is based on a material constitutive equation expressed as:

$$\sigma_{ij}^{experiment} = c_{ijkl}(a^{overall})\varepsilon_{kl}^{experiment}(a^{overall})$$

25 where i, j, k, l represent index of principal directions in the principal coordinate system, $$\sigma_{ij}^{experiment}$$

represents the experimental stress, $\varepsilon_{kl}$ represents the experimental strain, $c_{ijkl}(a^{overall})$ represents a weakly-oriented overall stiffness coefficient tensor, and $a^{overall}$ represents an overall effective orientation tensor under comprehensive influences of warpage.

7. The system of claim 6, wherein determining, via the simulation software, the orientation-calibrated experimental strain at the transverse direction and the orientation-calibrated experimental strain at the parallel direction according to the orientation-calibrated experimental stress at the transverse direction and the orientation-calibrated experimental stress at the parallel direction, respectively, is based on a fully-oriented material constitutive equation expressed as:

$$\varepsilon_{IJ}^{experiement} = s_{IJKL}\sigma_{KL}^{experiement}$$

where I, J, K, L represent index of principal directions in the pseudo principal coordinate system in the fully-aligned orientation state, $s_{IJKL}$ represents a fully-aligned overall compliance coefficient tensor.

8. The system of claim 1, wherein deriving, via the simulation software, the characteristic stress in the principal coordinate system from the characteristic strain is based on a material constitutive equation expressed as:

$$\sigma_{ij}^{\Pi} = c_{ijkl}(a^{overall})\varepsilon_{kl}^{\Pi}(a^{\Pi})$$

where i, j, k, l represent index of principal directions in the principal coordinate system, $$\sigma_{ij}^{\Pi}$$

represents the characteristic stress, $$\varepsilon_{kl}^{\Pi}$$

represents the characteristic strain, $c_{ijkl}(a^{overall})$ represents a weakly-oriented overall stiffness coefficient tensor, and $a^{overall}$ represents an overall effective orientation tensor under comprehensive influences of warpage.

9. The system of claim 8, wherein determining, via the simulation software, the orientation-calibrated characteristic strain at the transverse direction and the orientation-calibrated characteristic strain at the parallel direction according to the orientation-calibrated characteristic stress at the transverse direction and the orientation-calibrated characteristic stress at the parallel direction, respectively, is based on a fully-oriented material constitutive equation expressed as:

$$\varepsilon_{IJ}^{\Pi} = s_{IJKL}\sigma_{KL}^{\Pi}$$

where I, J, K, L represent index of principal directions in the pseudo principal coordinate system in the fully-aligned orientation state, $s_{IJKL}$ represents a fully-aligned overall compliance coefficient tensor.

10. The system of claim 1, wherein:
the calibrated-simulated warping behavior data comprises a calibrated-simulated strain at the transverse direction and a calibrated-simulated strain at the parallel direction of the specimen under the predetermined molding condition; and
the conversion relationship defines a regression parameter of a characteristic effect constituting the calibrated-simulated strain at the transverse direction and/or the calibrated-simulated strain at the parallel direction.

11. The system of claim 10, wherein:
when the characteristic effect is a thermal-induced effect, the regression parameter corresponds to a calibrated thermal property of a material of the specimen;
when the characteristic effect is a pressure-induced effect, the regression parameter corresponds to a calibrated pressure distribution of a material of the specimen;
when the characteristic effect is a crystalline-induced effect, the regression parameter corresponds to a calibrated crystalline shrinkage of a material of the specimen; and/or
when the characteristic effect is a flow-induced effect, the regression parameter corresponds to a calibrated flow-induced residual stress of a material of the specimen.

12. The system of claim 1 for predicting warping behavior in a product, wherein the specimen comprises at least one material selected from the group consisting of polypropylene, polyethylene, high-density polyethylene, low-density polyethylene, polystyrene, polyvinyl chloride, acrylonitrile-butadiene-styrene copolymer resin, polyoxymethylene, polycarbonate, polyamine, thermoplastic elastomer, epoxy resin, phenolic resin, unsaturated polyester, silicone, nitrile rubber, polyethyleneimine, polyethylene terephthalate, poly-lactic acid, and polyhydroxyalkanoate, Polyetherketone, liquid crystal polymer, modified polyphenylene ether, polyphenylene sulfide, nylon resin, and acrylic resin.

* * * * *